United States Patent [19]

Garner, Jr.

[11] Patent Number: 4,908,105
[45] Date of Patent: Mar. 13, 1990

[54] FLOW-COMPENSATED ELECTROCHEMICAL CELL AND METHOD OF ANALYSIS

[75] Inventor: William Garner, Jr., Austin, Tex.

[73] Assignee: Hydrolab Corporation, Austin, Tex.

[21] Appl. No.: 703,677

[22] Filed: Feb. 15, 1985

[51] Int. Cl.$^4$ .................. G01N 27/30; G01N 27/50
[52] U.S. Cl. ...................... 204/1 T; 204/406; 204/411; 204/412; 204/414; 204/415
[58] Field of Search ............... 204/411, 412, 415, 403, 204/1 P, 414, 406; 128/635

[56] References Cited

U.S. PATENT DOCUMENTS

| | | | |
|---|---|---|---|
| 768,818 | 8/1904 | Nelson | 204/242 X |
| 3,242,729 | 3/1966 | Keller | 204/411 X |
| 3,328,277 | 6/1967 | Solomons et al. | 204/412 |
| 3,403,090 | 9/1968 | Tajiri et al. | 204/422 X |
| 3,985,633 | 10/1976 | Lubbers et al. | 204/412 |
| 4,324,257 | 4/1982 | Albarda et al. | 128/635 |
| 4,333,473 | 6/1982 | Eberhard et al. | 128/635 |

OTHER PUBLICATIONS

Polarographic Oxygen Sensor by Irving Fatt, CRC Press, Inc., pp. 70–71, 162–167.
Oxygen Monitoring of Newborns by Skin Electrodes. Correlation Between Arerial and Cutaneously Determined PO$_2$ by Patrick Eberhard, Wolfgang Mindt, Franz Jann, and Konrad Hammacher from Oxygen Transport To Tissue, Plenum Press, pp. 1097–1101.
Routine Monitoring of the Arterial PO$_2$ of Newborn Infants By Continuous Registration of Transcutaneous PO$_2$ and Simultaneous Control of Relative Local Perfusion by Renate Huch, Dietrich W. Lubbers and Albert Huch, from Oxygen Transport To Tissue, Plenum Press, pp. 1121–1127, 1135.

*Primary Examiner*—G. L. Kaplan
*Attorney, Agent, or Firm*—Berman, Aisenberg & Platt

[57] ABSTRACT

A method and an apparatus for measuring concentration of a dissolved substance are disclosed. In accordance with the method, measurements are made with two instruments having different permeability characteristics to obtain two readings, and these readings are corrected in accordance with a pre-determined relationship. The apparatus provides an electrochemical cell wherein a common anode is surrounded by closely-spaced cathodes. The cathodes are in at least two groups, wherein the first group has a first response characteristic to the dissolved substance and the second group has a second response characteristic. In the preferred embodiment, the two characterisitcs are produced by providing different distances between a substance-selective membrane and respective cathodes. In one embodiment, the cathodes are annular and surround the anode at different radii, while in another embodiment the cathodes are discrete and are spaced from the anode by equal distances.

7 Claims, 3 Drawing Sheets

FLOW-COMPENSATED ELECTROCHEMICAL CELL AND METHOD OF ANALYSIS

TECHNICAL FIELD

This invention relates to the art of measurement of the concentration of substances. In particular, the invention relates to a method and an apparatus for flow-compensated measurement of dissolved oxygen.

BACKGROUND ART

It is frequently desirable to measure the concentration of a substance such as oxygen, in a liquid or a gas. For example, it may be desirable to measure the amount of dissolved oxygen in a river for environmental purposes or in an industrial process to monitor the process.

A typical instrument presently used for such a measurement is the Clark cell which is described in U.S. Pat. No. 2,913,386 (Clark, Jr.). The Clark cell is an electrochemical cell in which electrodes are surrounded by an electrolyte. A membrane separates the electrolyte from a liquid containing the substance to be measured, and the membrane selectively passes the substance to the electrolyte. A voltage is then applied between the electrodes, and the amount of the current in the electrode circuit is an indication of the concentration of the substance to be measured in the electrolyte. This is in turn a measure of the concentration of the substance in the liquid under study.

The term "Clark Cell" when used hereafter refers to the polarographic implementation as well as the galvanic implementation.

In the polarographic implementation, the anode is usually of silver, and the cathode is usually either gold or platinum. The electrolyte typically is a potassium chloride solution at neutral pH, although alkaline or acid salt solutions are occasionally used. In this system, an external voltage, nominally 800 millivolts, is applied to the cell to drive the reaction.

In the galvanic implementation, a typical anode metal is lead. The cathode is generally platinum. When the electrolyte is a highly alkaline solution, such as potassium hydroxide having a pH greater than about 13, the anode rises to 800 millivolts, and no external voltage need be applied.

The Clark cell suffers from several disadvantages, one of which is the fouling of the membrane. U.S. Pat. No. 4,168,220 (McAdam, et al.) proposes a solution to this fouling problem by providing two distinct types of electrochemical cells adjacent each other. A comparison of the readings of the two cells is an indication of the extent to which the membrane is fouled.

Another, more significant, problem with the Clark cell is its consumption of the substance which is being measured. A common use of the Clark cell is to measure dissolved oxygen, and the oxygen passes from the liquid under study through a hydrodynamic boundary layer between the main body of the liquid and the membrane, through the membrane, and then into the electrolyte. Upon application of an appropriate voltage to the electrodes, the oxygen is electrochemically reduced at the negative electrode. This reduction depletes oxygen in the electrolyte and causes more oxygen to flow through the boundary layer and through the membrane from the liquid under study.

In the steady state, the rate of reduction equals the rate of oxygen flow through the membrane. The common practice in the use of the Clark cell is to consider the rate of reduction to be a measure of the amount of oxygen in the liquid. The boundary layer introduces an error, however, because it impedes the flow of oxygen through the membrane. The amount by which the boundary layer impedes the oxygen flow is a function of the thickness of the boundary layer and is thus unpredictable.

The extent to which the boundary layer exists is a function of the flow velocity of the liquid under study. If the liquid is stagnant, a substantial boundary layer will be produced, thus causing a significant error in the measurements.

One prior art solution is to artificially cause the liquid to move with respect to the cell to reduce the size of the boundary layer. This movement is caused, for example, by stirring the liquid which requires additional expense and results in an extremely complicated instrument.

A second technique relies upon modifying the characteristics of the Clark cell so that its rate of oxygen consumption per unit membrane area is diminished, which has the effect of reducing the influence of the boundary layer. This technique suffers from the disadvantage that the resulting instrument responds very slowly to changes in the concentration of dissolved oxygen and is in many instances essentially useless.

SUMMARY OF THE INVENTION

In accordance with the invention, a modified Clark cell is provided wherein essentially two Clark cells having different response characteristics to the dissolved substance (preferably oxygen) in the presence of the boundary layers formed in the liquid under study are closely adjacent each other. The outputs from the cells are combined to eliminate the flow-sensitive characteristics of the cells resulting in a measurement which is not sensitive to the flow velocity. Furthermore, to the extent that membrane fouling is analogous to a hydrodynamic boundary layer, the cell according to the invention will be capable of correcting for the effect of fouling.

In a preferred embodiment, the new cell uses a common anode and two cathodes. One of the cathodes is spaced a first distance from the substance-selective membrane and the other cathode is placed a second distance from the membrane. The first and second cathodes are, in a first embodiment, concentric, with the common center lying on the centerline of the cell. In a second embodiment, the cathodes are discrete and are located in a geometric pattern whose center alternatively coincides with the centerline of the cell.

The response characteristic of the first cathode is varied with respect to that of the second cathode to result in two closely-spaced Clark cells having different responses to the substance being measured depending upon the motion of the liquid under study with respect to the cells. A preferred technique for altering the responses is to provide a first distance between the membrane and a first cathode, and a second distance between the membrane and the second cathode. In this embodiment, a common electrolyte is used to facilitate the use of a common anode. Alternatively, one can vary the permeability of the electrolyte surrounding one of the cathodes by using a distinct electrolyte or the membrane can have different permeabilities or thicknesses for respective cathodes. For example, one can add glycerin to an electrolyte to alter its viscosity to change its permeability. In another alternative, one can use two distinct Clark cells having different characteristics as long as these can be maintained close to each other. Ideally, the two cells occupy the same physical location so that they are subjected to identical portions of the liquid. This would ensure that the liquid affects both of the cells in an identical manner.

Because the physics of gas diffusion through the boundary layer, the membrane, and the electrolyte is the same for either the polarographic or galvanic implementation, the Applicant's inventive solution to the boundary layer problem is applicable to both types of Clark cells, as well as other cells having a boundary layer.

An object of this invention is to provide a method for measuring the concentration of a substance.

A further object of this invention is to provide a method whereby the concentration of a substance dissolved in a liquid may be measured in a manner which is independent of the flow velocity of the liquid.

Yet another object of this invention is to provide an apparatus for measuring a dissolved substance in a liquid which is insensitive to the flow velocity of the liquid.

Still another object of this invention is to provide an apparatus for measuring dissolved oxygen wherein a common anode is surrounded by a plurality of cathodes having different response characteristics to the dissolved oxygen in the liquid under study, depending upon the motion of the liquid.

DETAILED DESCRIPTION OF THE INVENTION

Figure 1:
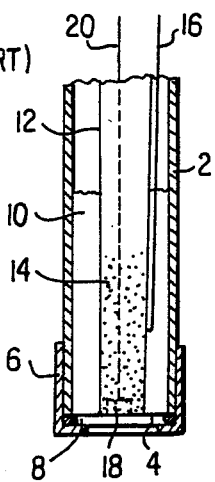
FIG. 1 is a partial cross section of a prior art cell.

FIG. 1 shows an electrochemical cell for determining the concentration of a substance in a liquid in accordance with the prior art. This cell is of the type known as a Clark cell and is described in U.S. Pat. No. 2,913,386. A generally tubular body 2 is closed at one end by a membrane 4. The membrane 4 is held to the end of tube 2 by a cap 6, and an O-ring 8 is placed between the cap 6 and the membrane 4 to provide a resilient force to hold the membrane in place. The interior of the tube 4 is filled with an electrolyte 10. A column 12 extends along the axis of the body 2 and is made of insulating material. A bottom portion 14 of the column 12 is covered with a metal to provide an anode. A conductor 16 is connected to the anode to provide electrical contact therewith. A cathode 18 is placed at the bottom of column 12 adjacent the membrane 4, and a conductor 20 provides an electrical connection with the cathode 18.

When the cell shown in FIG. 1 is placed in a liquid, the membrane 4 selectively passes a substance under study from the liquid into the electrolyte 10. An appropriate voltage is then applied to conductors 16 and 20, and electrical current develops. The size of the current is a function of the concentration of the substance under study in the electrolyte 10, and the Clark Jr. patent shows a suitable electronic circuit. The concentration of the substance in the electrolyte 10 is in turn a function of the concentration of the substance in the liquid being studied.

If the substance being studied is oxygen, the membrane 4 may be polyethylene, a material which passes oxygen to the electrolyte 10 and forms a barrier to other substances. The electrolyte 10 is provided to support the flow of current between the anode and the cathode. Dissolved oxygen in the electrolyte is reduced at the cathode. This reaction requires electrons resulting in a current flowing between the anode and the cathode.

Figure 2:
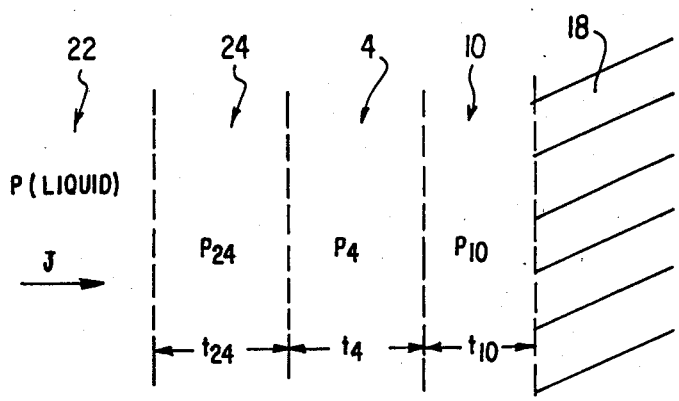
FIG. 2 is a diagram showing the relevant layers in an electrochemical cell.

FIG. 2 is a diagrammatic representation of an aspect of the cell shown in FIG. 1 and is useful for describing the problem solved by the Applicant, and the solution. A liquid 22 is under study, and boundary layer 24 develops adjacent the membrane 4, the thickness of the boundary layer being dependent upon the velocity of the liquid parallel to the membrane. The boundary layer tends to impede, in proportion to its thickness, the flow of a substance, such as oxygen, from the bulk of the liquid to the membrane. The oxygen is consumed by electrochemical reduction at the cathode at a rate in proportion to the rate of oxygen flow through the membrane. The rate of flow through the membrane is a function of the thickness of the boundary layer, and this results in a reduction in the rate of oxygen flow through the membrane to at least some degree. The degree to which the flow rate is reduced is a function of the velocity of flow of the liquid 22 past the cell, the oxygen permeability of the membrane 4, and the oxygen permeability of electrolyte 10. It will be appreciated from FIG. 2 that oxygen must flow from the liquid 22 through the boundary layer 24, the membrane 4, and the electrolyte 10 to reach the cathode 18.

In the steady state, conservation of mass requires that the amount of oxygen passing through each layer is equal to that passing through the other layers and will be represented by the symbol "J". The partial pressure of the oxygen in the liquid 22 will be represented by "p(liquid)", and since the partial pressure at the cathode is zero, because of the electrochemical reaction, the sum of the pressure drops across layers 24, 4, and 10 will be equal to p(liquid). The thickness of each layer is represented by the symbol "t", the oxygen permeability of each layer is represented by the symbol "P" and the partial pressure of oxygen is represented by "p." The subscript to each of these symbols refers to the particular layer.

When a gas diffuses through a permeable membrane, the decrease in gas pressure across the membrane may be represented by the following relationship:

$$p = Jt/P \tag{1}$$

As the gas flows through the three boundary layers shown in FIG. 2, equation (1) becomes:

$$p_{24} + p_4 + p_{10} = Jt_{24}/P_{24} + Jt_4/P_4 + Jt_{10}/P_{10} \tag{2}$$

Since the sum of the pressures across the three layers is the total partial pressure of the substance in the liquid, and since J is the same for all three membranes, this equation may be solved for J and rewritten as:

$$J = p(\text{liquid}) / (t_{24}/P_{24}) + (t_4/P_4) + (t_{10}/P_{10}) \tag{3}$$

It should be noted that J also represents the total gas flux reduced per unit area of the cathode.

As explained above, the thickness $t_{24}$ of boundary layer 24 will vary depending upon the velocity of the liquid past the end of the cell. If the liquid is stagnant, the thickness of this layer may grow to be substantial, thus providing a substantial barrier to the passage of oxygen. If the liquid is flowing rapidly, the thickness of this layer will reduce and will become negligible when compared to the thicknesses of layers 4 and 10.

Figure 3:
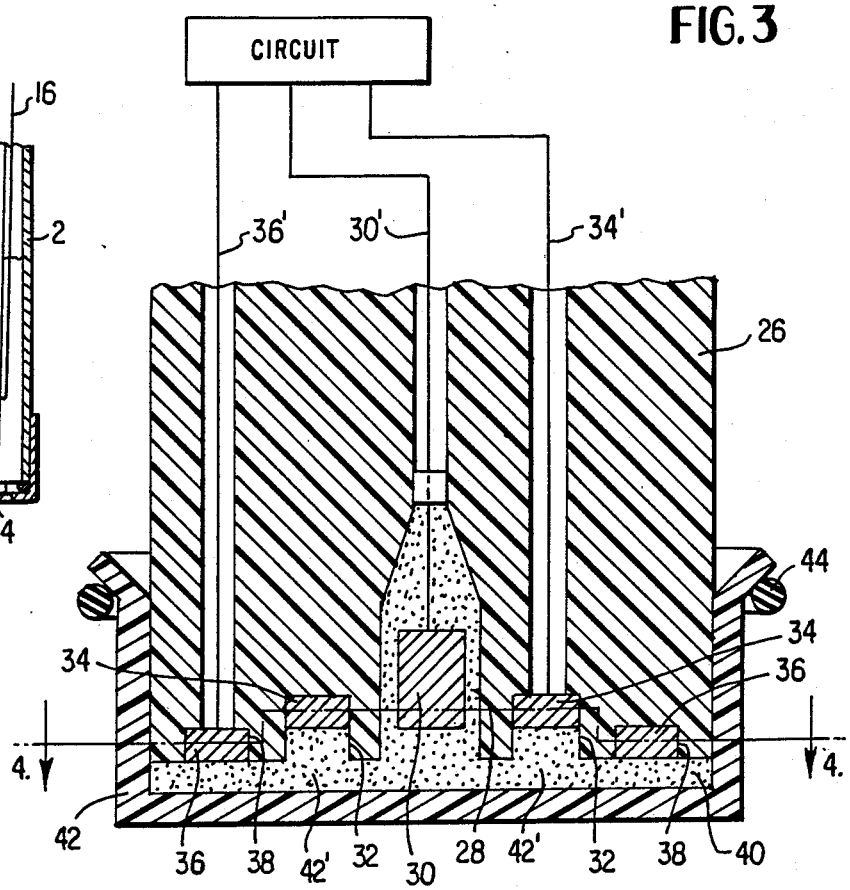
FIG. 3 is a partial cross section of a cell in accordance with the invention.

Applicant has discovered that the problem associated with the boundary layer 24 may be obviated by using at least two cells having different characteristics. With reference to FIG. 3, a preferred embodiment of the invention includes a cell body 26 with a first recess 28 for receiving an anode 30. A second recess 32 receives a first cathode 34, and a second cathode 36 is placed in a third recess 38. An electrolyte 40 fills the three recesses and is in electrical communication with the anode and the cathodes. A substance-selective membrane 42, such as polyethylene, is placed over the end of body 26 to form a chamber containing the electrolyte, and the membrane is illustratively secured to the body 26 by an O-ring 44.

Figure 4:
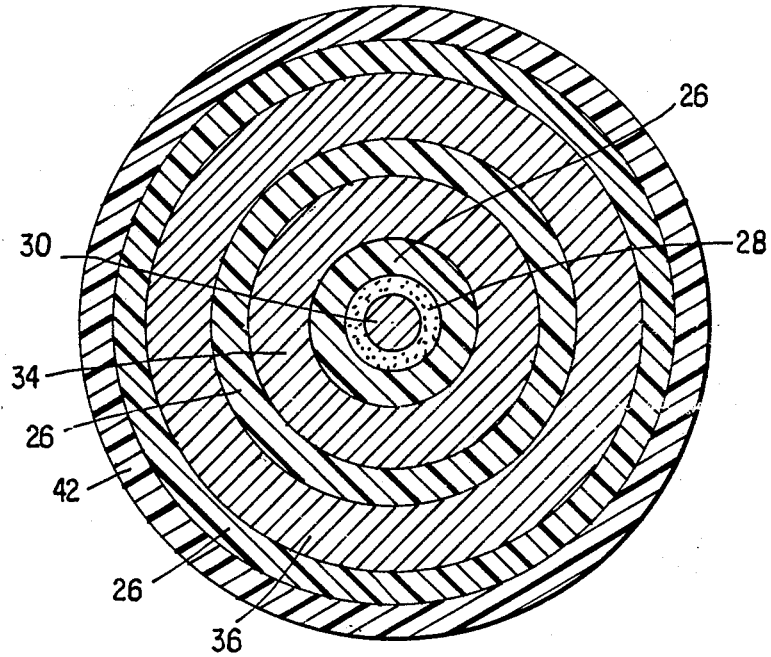
FIG. 4 is a partial cross section taken along line 4—4 of FIG. 3.

FIG. 4 shows a cross section taken along line 4—4 of FIG. 3 and illustrates the annular nature of cathodes 34 and 36. This arrangement provides, in a single instrument, two cells wherein the cathodes are extremely close to each other to thus "see" the same liquid. It will be appreciated from the discussion below that an important aspect of the cell shown in FIG. 3 is that the second recess 32 is deeper than the third recess 38 to produce an electrolyte layer between membrane 42 and cathode 34 which is thicker than the electrolyte layer between membrane 42 and cathode 36.

Electrical connection to anode 30 is made by conductor 30'; electrical connection is made with cathode 36 by conductor 36'; electrical connection is made with cathode 34 by conductor 34'.

The manner of operation of the instrument shown in FIGS. 3 and 4 will now be described.

As shown by equation (3), operation of a first cell "A" having a first set of characteristics may be described by:

$$J(A) = \frac{p(\text{liquid})}{tA_{24}/PA_{24} + tA_4/PA_4 + tA_{10}/PA_{10}} \quad (4)$$

A second cell "B" may be described by:

$$J(B) = \frac{p(\text{liquid})}{tB_{24}/PB_{24} + tB_4/PB_4 + tB_{10}/PB_{10}} \quad (5)$$

Symbols "A" and "B" have been added to the previously-defined variables to represent those variables with respect to each of the individual cells.

If the liquid 22 is flowing rapidly, the thickness of boundary layer 24 will become very small and the factors $tA_{24}$ and $tB_{24}$ will become essentially zero. This is a limiting case, and the oxygen flow rates in the respective cells in this condition are represented by:

$$J(A^*) = \frac{p(\text{liquid})}{tA_4/PA_4 + tA_{10}/PA_{10}} \quad (6)$$

$$J(B^*) = \frac{p(\text{liquid})}{tB_4/PB_4 + tB_{10}/PB_{10}} \quad (7)$$

Equations (4) and (5) can be solved for $tA_{24}/PA_{24}$ and $tB_{24}/PB_{24}$ respectively. By assuming that the two cells will develop identical boundary layers, the results may be set equal to each other, and it can be shown that the following relationship obtains:

$$J(A^*) = J(A) \frac{1 - \frac{J(A^*)}{J(B^*)}}{1 - \frac{J(A)}{J(B)}} \quad (8)$$

According to equation (8), the zero-boundary layer value for the oxygen consumed at the cathode of cell "A" can be determined by knowing the values, $J(A)$ and $J(B)$, of two different cells having equal boundary layers and the ratio, $J(A^*)/J(B^*)$, of the zero-boundary values for the two cells.

The values $J(A)$ and $J(B)$ can be directly determined by measuring current flowing between anode 30 and respective cathodes 34 and 36 in the instrument of FIG. 3. Any suitable circuit may be used for each of these measurements, such as that shown in the Clark, Jr. patent.

The ratio of zero-boundary layer values can be determined during calibration. For example, a sample of known oxygen content and very large permeability, such as air can be measured with the cell of FIG. 3. Alternatively, a liquid of known oxygen content may be vigorously stirred and its oxygen measured with the cell of FIG. 3. In either case, the ratio $J(A^*)/J(B^*)$ will be determined.

Once the instrument has been calibrated, one need only correct the cell readings $J(A)$ and $J(B)$ by the relationship expressed in equation (8) to obtain a flow-insensitive reading. Any of several means, such as the circuit of FIG. 3, may be employed.

An alternative to the use of recesses for electrodes 34 is to provide a membrane of increased thickness adjacent these electrodes as shown schematically at 42' in FIG. 3 by dashed lines. The effect of a membrane of increased thickness for selected electrodes would be the same as that of an electrolyte of increased thickness.

In the above analysis differences between the electrodes, such as their effective sizes, were not considered and it was assumed that the electrodes have equal effective areas. It has been observed in practice, however, that an electrode can have an effective area quite different from its actual area. For example, a very small electrode spaced a significant distance from the membrane will have a much larger effective area than an electrode closer to the membrane because the dissolved gases can diffuse to the more-distance electrode on diagonal as well as normal paths. Thus, the cathode current will be that of a physically larger electrode for equal oxygen concentrations.

The differences between electrodes may be taken into account by modifying equation (8) to include a factor "G" as follows:

$$J(A^*) = J(A) \frac{1 - G\frac{J(A^*)}{J(B^*)}}{1 - G\frac{J(A)}{J(B)}} \quad (9)$$

If equation (9) is solved for G, the result is:

$$G = \frac{J(B^*)}{J(A^*)} \cdot \frac{\frac{J(A^*)}{J(A)} - 1}{\frac{J(B^*)}{J(B)} - 1} \quad (10)$$

It will first be appreciated that factor G compensates for different effective areas of cathodes A and B because the first quantity on the right side of equation (10) is the inverse of the zero-boundary layer responses, which will represent the inverse of the ratio of the effective areas.

But, factor G also compensates for the differences between the dynamic behaviors of the cells, as represented by the second quantity on the right side of equation (10). The ratios $J(A^*)/J(A)$ and $J(B^*)/J(B)$ both increase from unity (i.e., zero boundary layer condition) to respective maximum values (i.e., a fully developed boundary layer). At unity values for these ratios, the second quantity becomes indeterminate. Thus, factor G can be evaluated for a particular arrangement of cells only if a boundary layer is present.

The second factor is less than unity if cell A is less affected by a boundary layer than is cell B. The original choice of which cell to call cell A is somewhat arbitrary, and it has been determined that an appropriate convention is for cell A to be defined as that cell which is less sensitive to a boundary layer than is cell B.

Factor G is best determined empirically by actual measurement of the values of equation (10) during calibration. Many such measurements have been made by Applicant and it has been determined that factor G is a function of the boundary layer thickness. Thus, factor G is not a single value but is a variable which can be measured during calibration. While the cathode areas may now be arbitrary, because factor G will make the necessary correction, experience has shown that the second factor of equation (10) should be made small to obtain a more accurate measurement. There are, of course, physical constraints on how small the second factor can be.

Once the factor G is known, a cell such as those shown in the drawings is used to make measurements, and the values are corrected to obtain the zero boundary layer value by use of equation (9).

Figure 5:
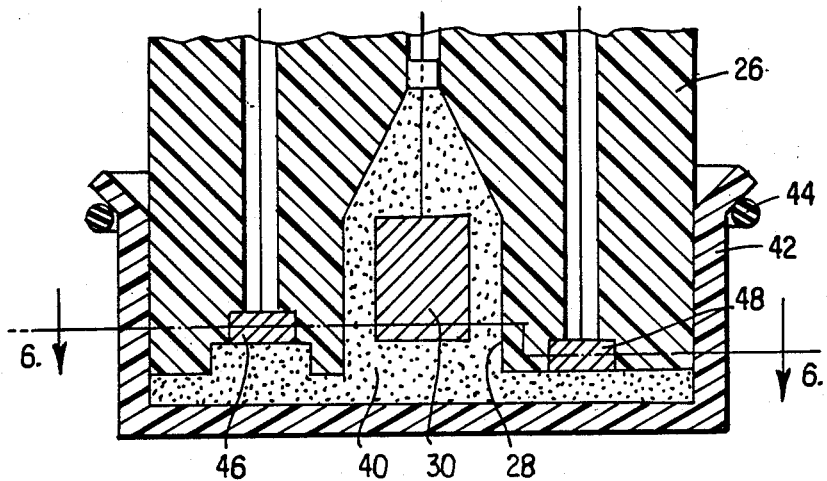
FIG. 5 is a partial cross section of a second embodiment of a cell in accordance with the invention.
Figure 6:
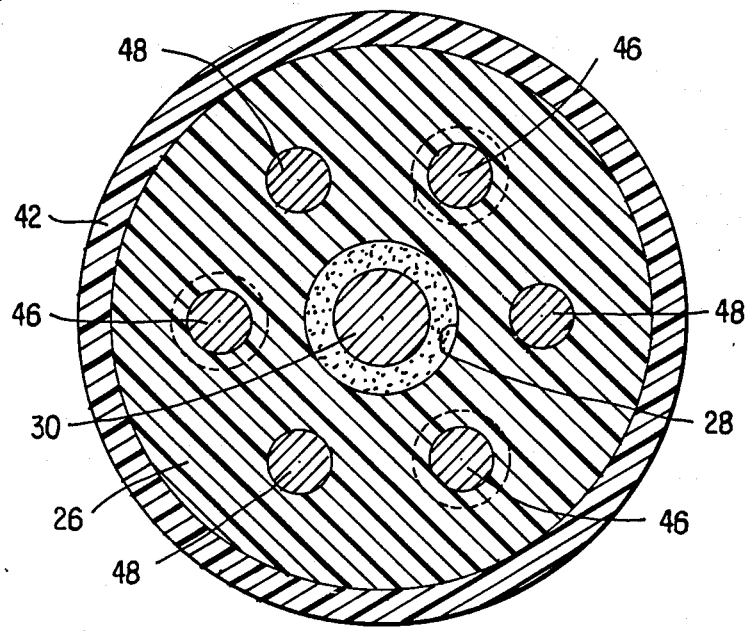
FIG. 6 is a cross section taken along line 6—6 of FIG. 5.

FIGS. 5 and 6 show a second embodiment of an instrument in accordance with the invention. Those elements which are identical to those shown in FIGS. 3 and 4 are identified by the same reference numerals. In the embodiment shown in FIGS. 5 and 6, the first and second cathodes are discrete, instead of annular, and are placed at equal distances from the center line of the cell. A first set of cathodes 46 is placed at a first distance from the membrane 42, while a second set of cathodes 48 is placed at a smaller distance from the membrane 42. This difference in spacing produces the two cells discussed above having different response characteristics. It will be appreciated that since the cathodes are close to each other, they will again "see" the same liquid 22.

The flow-compensation method described above is based upon processing output signals of two cells having dissimilar responses to the effects of the boundary layer between the cell membranes and a common fluid under investigation. Generally, the cell that is least affected by the boundary layer is also the slowest to respond to external changes. For instance, an abrupt change in boundary layer thickness or in the oxygen content of the fluid under investigation will be reflected almost immediately in the output signal of one cell (the one with the thinner membrane or electrolyte layer) but will be delayed in the other output signal. The slower signal is not only delayed but is also smoothed so that it resembles an electronically-filtered version of the faster signal. This effect has not proved to be a great difficulty, and good results have been obtained by simply filtering (delaying and smoothing) the faster signal before using it in the computation. Filter optimization is best accomplished by trial and error.

It will be appreciated that a flow-insensitive instrument and a method for making flow-independent measurements have been described. Modification of the invention within the scope of the appended claims will be apparent to those of skill in the art. For example, the described technique could be used to measure other boundary layer sensitive quantities, such as heat.

Further, the invention could be used to determine flow velocity of a fluid if the oxygen concentration is known.

What is claimed is:

1. An instrument for chemical analysis comprising body means for supporting a first electrode having a first polarity and a plurality of second electrodes having a second polarity with respect to said first electrode, and electrolyte means for passing electrical current between said first and second electrodes wherein the rate of passage of a substance to at least one of said second electrodes is different from the rate of passage of said substance to another of said second electrodes, and computation means connected to said first and second electrodes for combining signals from each of said second electrodes and correcting said signals to produce a single flow-insensitive output representative of said substance.

2. A method for chemical analysis comprising providing a first electrochemical cell for measuring concentration of a substance in a medium and having a first flow sensitivity to the velocity of flow of said medium past said first cell and a second electrochemical cell for measuring the concentration of said substance in said medium and having a second flow sensitivity to the velocity of flow of said medium past said second cell, placing said first and second cells in said medium in close proximity to each other and combining values representative of the concentration of the substance produced by each of said cells to provide a measurement of said concentration which is not sensitive to said velocity of flow.

3. A method according to claim 2 wherein said first electrochemical cell and said second electrochemical cell have a common anode.

4. A method according to claim 2 wherein said step of using values from each of said cells comprises the step of modifying said values by a value derived from the ratio of the values from each cell as well as the ratio of the zero boundary layer values for each of the cells.

5. A method for analysis of a flowing medium comprising providing a first measurement means for measuring a quantity of said medium and having a first flow sensitivity to the velocity of flow of said medium and a second measurement means for measuring said quantity in said medium and having a second flow sensitivity to said velocity of flow of said medium, placing said first and second measurement means in close proximity to each other, and combining the measured values of said quantity produced by said first and second measurement means to determine the actual amount of said quantity.

6. A method for measuring the concentration of a dissolved substance in a sample comprising providing an electrochemical cell comprising a first electrode of one polarity, second and third electrodes at an opposite polarity, and a membrane for passing said substance from said sample to said electrodes, said second and third electrodes being so positioned that said substance travels at different rates to each of said second and third electrodes, said method further comprising measuring the electrical current through each of said second and third electrodes to produce signals representative of said concentration and combining and correcting said signals in accordance with a calibration value to produce a measurement of said concentration.

7. A method according to claim 6 wherein said calibration value is a function of the ratio of zero boundary layer signals for said electrodes.

* * * * *